United States Patent
Marini

(10) Patent No.: US 6,821,524 B2
(45) Date of Patent: Nov. 23, 2004

(54) COSMETIC SKIN CARE COMPOSITIONS

(75) Inventor: Jan L. Marini, San Jose, CA (US)

(73) Assignee: Jan Marini Skin Research, Inc., San Jose, CA (US)

( * ) Notice: Subject to any disclaimer, the term of this patent is extended or adjusted under 35 U.S.C. 154(b) by 151 days.

(21) Appl. No.: 10/161,884

(22) Filed: Jun. 3, 2002

(65) Prior Publication Data

US 2003/0228266 A1 Dec. 11, 2003

(51) Int. Cl.⁷ .............................. A61K 7/42; A61K 7/44; A61K 7/00; A61K 38/00
(52) U.S. Cl. .......................... 424/401; 424/59; 424/60; 424/400; 514/12; 514/937; 514/938
(58) Field of Search .......................... 424/59, 60, 400, 424/401; 514/12

(56) References Cited

U.S. PATENT DOCUMENTS

| 4,297,276 A | 10/1981 | Goldstein et al. |
| 6,328,987 B1 | 12/2001 | Marini |
| 6,602,519 B1 * | 8/2003 | Stevenson et al. .......... 424/451 |

OTHER PUBLICATIONS

Malinda et al. (1999) *J. Invest. Dermatol.*, 113:364–368.
Roberts and Palade (1995) *J. Cell Sci.*, 108:2369–2379.
Genbank, accession No. NM_003376.
Knighton et al. (1990) *J. Trauma*, 30:S134–144.
Genbank, accession No. X02812 J05114.

* cited by examiner

Primary Examiner—Shelley A. Dodson
(74) Attorney, Agent, or Firm—Pamela J. Sherwood; Bozicevic, Field, & Francis LLP

(57) ABSTRACT

Cosmetic skin care compositions containing thymosin beta 4 are provided. The compositions improve the appearance of aged or damaged skin.

13 Claims, No Drawings

COSMETIC SKIN CARE COMPOSITIONS

BACKGROUND OF THE INVENTION

Maintaining a youthful appearance is of great importance to many people, particularly in an aging population. Several of the visible signs of aging result from its effects on the skin. The passage of time is reflected in the appearance of wrinkles and fine lines; by a slackening of tissue; a loss of cutaneous elasticity; a leathery or dry appearance; and by the yellowing of the skin which becomes duller and loses its radiance. Skin that has been consistently exposed to sunlight throughout life, particularly the face and hands, may show pigmentation marks, telangiectasia and elastosis. At the histological level, skin damage from photoaging is shown in tangled, thickened, abnormal elastic fibers, decreased collagen and increased glycosaminoglycan content. The aging process also results in thinning and deterioration of the skin. There is a reduction in cells and in blood supply, and a flattening in the junction between the dermis and epidermis.

Treatments designed to prolong or promote youthful appearance include topical applications of cosmetic preparations, lotions and moisturizer, electrical stimulation, collagen injections and cosmetic surgery. However, there is still a serious need for skin care compositions that treat wrinkles and fine lines, and restore the youthful appearance of the skin.

SUMMARY OF THE INVENTION

The present invention features novel cosmetic skin care compositions for treating wrinkles and fine lines; firming skin tissue; and reviving the radiance of the skin. The skin care compositions comprise thymosin beta 4 (TB4) at a concentration of from about at a concentration of from about 1 ng/ml to about 10 µg/ml, and a cosmetically acceptable vehicle. This invention also features methods for the treatment of wrinkles and fine lines; firming skin tissue; and reviving the radiance of the skin, comprising topically applying thereto a cosmetic skin care composition containing TB4 at a concentration of from about 1 ng/ml to about 10 µg/ml. Preferably the cosmetic care compositions of the invention further comprise human transforming growth factor β1 (TGFB1), at a concentration of from about 5 pg/ml to 1 µg/ml; and may also comprise human vascular endothelial growth factor (VEGF), at a concentration of from about 1 pg/ml to 1 µg/ml.

DETAILED DESCRIPTION OF THE EMBODIMENTS

Topical compositions are provided for the treatment of wrinkles and fine lines; firming skin tissue; and reviving the radiance of the skin. The skin care compositions comprise thymosin beta 4 (TB4) at a concentration of from about at a concentration of from about 1 ng/ml to about 10 µg/ml, and a cosmetically acceptable vehicle, and may further comprise human TGFB1 and/or human VEGF.

Thymosin-beta-4 (TB4) is a small polypeptide that inhibits the migration of macrophages, and stimulates the secretion of hypothalamic luteinizing hormone-releasing hormone. It has also been implicated in wound healing, (see Malinda et al. (1999) J. Invest. Dermatol. 113:364–368). The molecule is ubiquitous; it had been found in all tissues and cell lines analyzed, but is found in highest concentrations in spleen, thymus, lung, and peritoneal macrophages. The polypeptide sequence of TB4 may be found in U.S. Pat. No. 4,297,276, Goldstein et al. The corresponding genetic sequence is described by Gondo et al. (1987) J. Immunol. 139 (11), 3840–3848, Genbank accession number M17733. Preferably human recombinant TB4 is used, which is commercially available, e.g. from Advanced ChemTech, Inc. (Louisville, Ky.), at a specific activity of 5 mg/1000 U. In the compositions of the present invention, the TB4 is used at a concentration of at least about 1 ng/ml, usually at least about 10 ng/ml, more usually at least about 100 ng/ml, and not more than about 10 µg/ml, more usually not more than about 1 µg, and may be used at a concentration of about 0.1 to 0.5 µg/ml.

Vascular endothelial growth factor (VEGF) is a mitogenic primarily for vascular endothelial cells. It may be a major regulator of tumor angiogenesis in vivo. It has been reported that VEGF increases the permeability of blood vessels (Roberts and Palade (1995) J. Cell Sci. 108:2369–2379). The polypeptide sequence of human VEGF and corresponding genetic sequence may be found in Genbank, accession number NM_003376. Recombinant human VEGF is commercially available, e.g. from R&D Systems (Minneapolis, Minn.), at a specific activity of 50 µg/1000U. In the compositions of the present invention, when present VEGF is used at a concentration of at least about 0.001 ng/ml, usually at least about 0.01 ng/ml, more usually at least about 0.1 ng/ml, and not more than about 1 µg/ml, usually not more than about 0.1 µg/ml, and may be used at a concentration of from 1 to 5 ng/ml.

Transforming growth factor beta 1 (TGFB) is a multi-functional peptide that controls proliferation, differentiation, and other functions in many cell types. Many cells synthesize TGFB and almost all of them have specific receptors for this peptide. The effect of TGFB on wound healing angiogenesis has been explored by Knighton et al. (1990) J. Trauma 30:S134–144. The polypeptide sequence of human TGFB and corresponding genetic sequence may be found in Genbank, accession number X02812 J05114, Derynck et al. (1985) Nature 316 (6030), 701–705. Recombinant human TGFB is commercially available, e.g. from R&D Systems (Minneapolis, Minn.), at a specific activity of 20 µg/1000 U. In the compositions of the present invention, when present TGFB1 is used at a concentration of at least about 5 pg/ml, usually at least about 50 pg/ml, more usually at least about 0.1 ng/ml, and not more than about 1 µg/ml, usually not more than about 100 ng/ml, more usually not more than about 10 ng/ml, and may be used at a concentration of from about 0.1 to 1 ng/ml.

For use in the present invention these proteins variants and active fragments of these proteins, as known in the art, may be used. The proteins may be produced from eukaryotic or prokaryotic cells by recombinant methods, isolated from cells in a native form, or may be synthesized in vitro as known in the art.

The compositions of the invention find use in improving the appearance of fine lines and wrinkles, e.g. in sun-damaged skin, etc. The compositions may also be used in the treatment of irritated skin, e.g. minor rashes and burns. Further examples of minor skin irritations include acne, cold sores, dry skin, sunburn, insect bites and other inflammatory and non-inflammatory lesions of the skin.

Optional Skin Benefit Materials and Cosmetic Adjuncts

The compositions of the invention may optionally comprise other skin benefit materials. These include estradiol; progesterone; pregnanalone; coenzyme Q10; methylsolanomethane (MSM); copper peptide (copper extract); plankton extract (phytosome); glycolic acid; kojic acid; ascorbyl palmitate; all-trans-retinol; azaleic acid; salicylic acid; broparoestrol; estrone; adrostenedione; androstanediols; etc. The steroids will generally present at a concentration of less than about 2% of the total by weight of the composition, while the other skin benefit materials may be present at higher levels, for example as much as 10 to 15%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used. The exact amount of sunscreen employed in the compositions can vary depending upon the degree of protection desired from the sun's UV radiation.

Cosmetically Acceptable Vehicle

The compositions of the invention comprise a cosmetically acceptable vehicle to act as a dilutant, dispersant or carrier for TB4, so as to facilitate its distribution when the composition is applied to the skin. Vehicles other than or in addition to water can include liquid or solid emollients, solvents, humectants, thickeners and powders.

The cosmetically acceptable vehicle will usually form from 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (OMI) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device. The product may be specifically formulated for use as a hand, or as a facial treatment.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates topical compositions according to the present invention. The compositions can be processed in conventional manner. They are suitable for cosmetic use. In particular the compositions are suitable for application to wrinkled, rough, flaky, aged and/or UV-damaged skin and/or dry skin and post-menopausal skin to improve the appearance and the feel thereof as well as for application to healthy skin to prevent or retard deterioration thereof.

| OIL-IN-WATER EMULSIONS | | | | | |
|---|---|---|---|---|---|
| TB4 only | | TB4 + TGFB1 | | TB4 + TGFB1 + VEGF | |
| Ingredient | % w/w | Ingredient | % w/w | Ingredient | % w/w |
| Carbomer | 0.30 | Carbomer | 0.30 | Carbomer | 0.30 |
| Disodium EDTA | 0.10 | Disodium EDTA | 0.10 | Disodium EDTA | 0.10 |
| Glycerin | 3.00 | Glycerin | 3.00 | Glycerin | 3.00 |
| Polysorbate 20 | 2.50 | Polysorbate 20 | 2.50 | Polysorbate 20 | 2.50 |
| Butylene Glycol | 2.00 | Butylene Glycol | 2.00 | Butylene Glycol | 2.00 |
| Methylparaben | 0.30 | Methylparaben | 0.30 | Methylparaben | 0.30 |
| Triethanolamine 99% | 0.30 | Triethanolamine 99% | 0.30 | Triethanolamine 99% | 0.30 |
| Isopropyl Myristate | 5.00 | Isopropyl Myristate | 5.00 | Isopropyl Myristate | 5.00 |
| Octyl Palmitate | 3.00 | Octyl Palmitate | 3.00 | Octyl Palmitate | 3.00 |
| Cetyl Alcohol | 1.00 | Cetyl Alcohol | 1.00 | Cetyl Alcohol | 1.00 |
| Dimethicone 100 cst | 0.50 | Dimethicone 100 cst | 0.50 | Dimethicone 100 cst | 0.50 |
| Beeswax | 0.30 | Beeswax | 0.30 | Beeswax | 0.30 |
| Propylparaben | 0.10 | Propylparaben | 0.10 | Propylparaben | 0.10 |
| Germall II | 0.10 | Germall II | 0.10 | Germall II | 0.10 |
| Fragrance | 0.10 | Fragrance | 0.10 | Fragrance | 0.10 |
| recombinant human TB4 | 2.5 µg/ml | recombinant human TB4 | 2.5 µg/ml | recombinant human TB4 | 2.5 µg/ml |
| | | recombinant human TGFB1 | 0.5 ng/ml | recombinant human TGFB1 | 0.5 ng/ml |
| | | | | recombinant human VEGF | 0.2 ng/ml |
| di water as required | | di water as required | | di water as required | |
| Total | 100.00 | Total | 100.00 | Total | 100.00 |

| OIL-IN-WATER EMULSION | | | | | |
|---|---|---|---|---|---|
| TB4 only | | TB4 + TGFB1 | | TB4 + TGFB1 + VEGF | |
| Ingredient | % w/w | Ingredient | % w/w | Ingredient | % w/w |
| Xanthan Gum | 0.20 | Xanthan Gum | 0.20 | Xanthan Gum | 0.20 |
| Disodium EDTA | 0.10 | Disodium EDTA | 0.10 | Disodium EDTA | 0.10 |
| Glycerin | 5.00 | Glycerin | 5.00 | Glycerin | 5.00 |

-continued

OIL-IN-WATER EMULSION

| TB4 only | | TB4 + TGFB1 | | TB4 + TGFB1 + VEGF | |
|---|---|---|---|---|---|
| Ingredient | % w/w | Ingredient | % w/w | Ingredient | % w/w |
| Butylene Glycol | 2.00 | Butylene Glycol | 2.00 | Butylene Glycol | 2.00 |
| Methylparaben | 0.30 | Methylparaben | 0.30 | Methylparaben | 0.30 |
| Isopropyl Myristate | 5.00 | Isopropyl Myristate | 5.00 | Isopropyl Myristate | 5.00 |
| Octyl Palmitate | 3.00 | Octyl Palmitate | 3.00 | Octyl Palmitate | 3.00 |
| Cetyl Alcohol | 1.00 | Cetyl Alcohol | 1.00 | Cetyl Alcohol | 1.00 |
| Dimethicone 100 cst | 0.50 | Dimethicone 100 cst | 0.50 | Dimethicone 100 cst | 0.50 |
| Steareth-2 | 0.40 | Steareth-2 | 0.40 | Steareth-2 | 0.40 |
| Steareth-21 | 3.00 | Steareth-21 | 3.00 | Steareth-21 | 3.00 |
| Propylparaben | 0.10 | Propylparaben | 0.10 | Propylparaben | 0.10 |
| Germall II | 0.10 | Germall II | 0.10 | Germall II | 0.10 |
| Fragrance | 0.10 | Fragrance | 0.10 | Fragrance | 0.10 |
| recombinant human TB4 | 2.5 µg/ml | recombinant human TB4 | 2.5 µg/ml | recombinant human TB4 | 2.5 µg/ml |
| | | recombinant human TGFB1 | 0.5 ng/ml | recombinant human TGFB1 | 0.5 ng/ml |
| | | | | recombinant human VEGF | 0.2 ng/ml |
| di water as required | | di water as required | | di water as required | |
| Total | 100.00 | Total | 100.00 | Total | 100.00 |

WATER-IN-OIL EMULSION

| TB4 only | | TB4 + TGFB1 | | TB4 + TGFB1 + VEGF | |
|---|---|---|---|---|---|
| Ingredient | % w/w | Ingredient | % w/w | Ingredient | % w/w |
| Disodium EDTA | 0.10 | Disodium EDTA | 0.10 | Disodium EDTA | 0.10 |
| Glycerin | 3.00 | Glycerin | 3.00 | Glycerin | 3.00 |
| Propylene Glycol | 2.00 | Propylene Glycol | 2.00 | Propylene Glycol | 2.00 |
| Sodium Chloride | 0.70 | Sodium Chloride | 0.70 | Sodium Chloride | 0.70 |
| Methylparaben | 0.30 | Methylparaben | 0.30 | Methylparaben | 0.30 |
| Cyclomethicone | 14.00 | Cyclomethicone | 14.00 | Cyclomethicone | 14.00 |
| Isopropyl Myristate | 5.00 | Isopropyl Myristate | 5.00 | Isopropyl Myristate | 5.00 |
| Octyl Palmitate | 3.00 | Octyl Palmitate | 3.00 | Octyl Palmitate | 3.00 |
| Dimethicone Copolyol | 2.50 | Dimethicone Copolyol | 2.50 | Dimethicone Copolyol | 2.50 |
| Dimethicone 100 cst | 0.50 | Dimethicone 100 cst | 0.50 | Dimethicone 100 cst | 0.50 |
| Beeswax | 0.30 | Beeswax | 0.30 | Beeswax | 0.30 |
| Propylparaben | 0.10 | Propylparaben | 0.10 | Propylparaben | 0.10 |
| Germall II | 0.10 | Germall II | 0.10 | Germall II | 0.10 |
| Fragrance | 0.10 | Fragrance | 0.10 | Fragrance | 0.10 |
| recombinant human TB4 | 2.5 µg/ml | recombinant human TB4 | 2.5 µg/ml | recombinant human TB4 | 2.5 µg/ml |
| | | recombinant human TGFB1 | 0.5 ng/ml | recombinant human TGFB1 | 0.5 ng/ml |
| | | | | recombinant human VEGF | 0.2 ng/ml |
| di water as required | | di water as required | | di water as required | |
| Total | 100.00 | Total | 100.00 | Total | 100.00 |

HYDRO-GEL

| TB4 only | | TB4 + TGFB1 | | TB4 + TGFB1 + VEGF | |
|---|---|---|---|---|---|
| Ingredient | % w/w | Ingredient | % w/w | Ingredient | % w/w |
| Butylene Glycol | 5.00 | Butylene Glycol | 5.00 | Butylene Glycol | 5.00 |
| PPG-5-Ceteth 20 | 5.00 | PPG-5-Ceteth 20 | 5.00 | PPG-5-Ceteth 20 | 5.00 |
| Glycerin | 3.00 | Glycerin | 3.00 | Glycerin | 3.00 |
| Carbomer | 1.20 | Carbomer | 1.20 | Carbomer | 1.20 |
| Triethanolamine 99% | 1.20 | Triethanolamine 99% | 1.20 | Triethanolamine 99% | 1.20 |
| Methylparaben | 0.30 | Methylparaben | 0.30 | Methylparaben | 0.30 |
| Polysorbate 20 | 0.25 | Polysorbate 20 | 0.25 | Polysorbate 20 | 0.25 |

-continued

HYDRO-GEL

| TB4 only | | TB4 + TGFB1 | | TB4 + TGFB1 + VEGF | |
|---|---|---|---|---|---|
| Ingredient | % w/w | Ingredient | % w/w | Ingredient | % w/w |
| Disodium EDTA | 0.10 | Disodium EDTA | 0.10 | Disodium EDTA | 0.10 |
| Germall II | 0.10 | Germall II | 0.10 | Germall II | 0.10 |
| recombinant human TB4 | 2.5 μg/ml | recombinant human TB4 | 2.5 μg/ml | recombinant human TB4 | 2.5 μg/ml |
| | | recombinant human TGFB1 | 0.5 ng/ml | recombinant human TGFB1 | 0.5 ng/ml |
| | | | | recombinant human VEGF | 0.2 ng/ml |
| di water as required | | di water as required | | di water as required | |
| Total | 100.00 | Total | 100.00 | Total | 100.00 |

ANHYDROUS SERUM

| TB4 only | | TB4 + TGFB1 | | TB4 + TGFB1 + VEGF | |
|---|---|---|---|---|---|
| Ingredient | % w/w | Ingredient | % w/w | Ingredient | % w/w |
| Cyclomethicone | 72.40 | Cyclomethicone | 72.40 | Cyclomethicone | 72.40 |
| Isopropyl Myristate | 5.00 | Isopropyl Myristate | 5.00 | Isopropyl Myristate | 5.00 |
| Octyl Palmitate | 3.00 | Octyl Palmitate | 3.00 | Octyl Palmitate | 3.00 |
| Polyglycerol-6 Dioleate | 5.00 | Polyglycerol-6 Dioleate | 5.00 | Polyglycerol-6 Dioleate | 5.00 |
| Butylene Glycol | 4.00 | Butylene Glycol | 4.00 | Butylene Glycol | 4.00 |
| Dimethicone 100 cst | 5.00 | Dimethicone 100 cst | 5.00 | Dimethicone 100 cst | 5.00 |
| Beeswax | 0.30 | Beeswax | 0.30 | Beeswax | 0.30 |
| Propylparaben | 0.20 | Propylparaben | 0.20 | Propylparaben | 0.20 |
| Fragrance | 0.10 | Fragrance | 0.10 | Fragrance | 0.10 |
| recombinant human TB4 | 2.5 μg/ml | recombinant human TB4 | 2.5 μg/ml | recombinant human TB4 | 2.5 μg/ml |
| | | recombinant human TGFB1 | 0.5 ng/ml | recombinant human TGFB1 | 0.5 ng/ml |
| | | | | recombinant human VEGF | 0.2 ng/ml |
| di water as required | | di water as required | | di water as required | |
| Total | 100.00 | Total | 100.00 | Total | 100.00 |

HYDRO-ALCOHOLIC GEL

| TB4 only | | TB4 + TGFB1 | | TB4 + TGFB1 + VEGF | |
|---|---|---|---|---|---|
| Ingredient | % w/w | Ingredient | % w/w | Ingredient | % w/w |
| Alcohol SDA40B | 30.00 | Alcohol SDA40B | 30.00 | Alcohol SDA40B | 30.00 |
| Butylene Glycol | 5.00 | Butylene Glycol | 5.00 | Butylene Glycol | 5.00 |
| PPG-5-Ceteth 20 | 5.00 | PPG-5-Ceteth 20 | 5.00 | PPG-5-Ceteth 20 | 5.00 |
| Glycerin | 3.00 | Glycerin | 3.00 | Glycerin | 3.00 |
| Carbomer | 1.20 | Carbomer | 1.20 | Carbomer | 1.20 |
| Triethanolamine 99% | 1.20 | Triethanolamine 99% | 1.20 | Triethanolamine 99% | 1.20 |
| 4-chromanone | 1.00 | 4-chromanone | 1.00 | 4-chromanone | 1.00 |
| Methylparaben | 0.30 | Methylparaben | 0.30 | Methylparaben | 0.30 |
| Polysorbate 20 | 0.25 | Polysorbate 20 | 0.25 | Polysorbate 20 | 0.25 |
| Disodium EDTA | 0.10 | Disodium EDTA | 0.10 | Disodium EDTA | 0.10 |
| Germall II | 0.10 | Germall II | 0.10 | Germall II | 0.10 |
| recombinant human TB4 | 2.5 μg/ml | recombinant human TB4 | 2.5 μg/ml | recombinant human TB4 | 2.5 μg/ml |
| | | recombinant human TGFB1 | 0.5 ng/ml | recombinant human TGFB1 | 0.5 ng/ml |
| | | | | recombinant human VEGF | 0.2 ng/ml |
| di water as required | | di water as required | | di water as required | |
| Total | 100.00 | Total | 100.00 | Total | 100.00 |

What is claimed is:

1. A cosmetic composition for topical treatment of skin, comprising from 0.1 ng/ml to 1 µg/ml of human thymosin β4; and a cosmetically acceptable vehicle.

2. A cosmetic composition for topical treatment of skin, comprising from 0.1 ng/ml to 1 µg/ml of human thymosin β4; human transforming growth factor β1 at a concentration from 5 pg to 1 µg/ml, and a cosmetically acceptable vehicle.

3. A cosmetic composition for topical treatment of skin, comprising from 0.1 ng/ml to 1 µg/ml of human thymosin β4; human vascular endothelial growth factor at a concentration from 1 pg/ml to 1 µg/ml and a cosmetically acceptable vehicle.

4. The composition according to claim 3, and further comprising one or more of estradiol, progesterone; pregnanalone; coenzyme Q10; methylsolanomethane (MSM); copper peptide (copper extract); plankton extract (phytosome); glycolic acid; kojic acid; ascorbyl palmitate; all trans retinol; azaleic acid; salicylic acid; broparoestrol; estrone; adrostenedione; and androstanediol.

5. The composition according to claim 3, wherein said composition further comprises a sunblock.

6. The composition according to claim 3, wherein said cosmetically acceptable vehicle is an oil in water, or water in oil emulsion.

7. A method for improving the appearance of the skin, the method comprising:

applying topically a cosmetic composition comprising from 0.1 ng/ml to 1 µg/ml of human thymosin β4; and a cosmetically acceptable vehicle.

8. A method for improving the appearance of the skin, the method comprising:

applying topically a cosmetic composition comprising from 0.1 ng/ml to 1 µg/ml of human thymosin β4, human transforming growth factor β1 at a concentration from 5 pg to 1 µg/ml, and a cosmetically acceptable vehicle.

9. A method for improving the appearance of the skin, the method comprising:

applying topically a cosmetic composition comprising from 0.1 ng/ml to 1 µg/ml of human thymosin β4, human vascular endothelial growth factor at a concentration from 1 pg/ml to 1 µg/ml, and a cosmetically acceptable vehicle.

10. The method according to claim 9, wherein said skin is aged, photoaged, dry, lined or wrinkled skin.

11. The method according to claim 10, wherein said composition further comprises one or more of estradiol; progesterone; pregnanalone; coenzyme Q10; methylsolanomethane (MSM); copper peptide (copper extract); plankton extract (phytosome); glycolic acid; kojic acid; ascorbyl palmitate; all trans retinol; azaleic acid; salicylic acid; broparoestrol; estrone; adrostenedione; and androstanediols.

12. The method according to claim 10, wherein said composition further comprises a sunblock.

13. The method according to claim 10, wherein said cosmetically acceptable vehicle is an oil in water, or water in oil emulsion.

* * * * *